(12) United States Patent
Kolarovic et al.

(10) Patent No.: US 6,679,830 B2
(45) Date of Patent: Jan. 20, 2004

(54) INFANT INCUBATOR WITH NON-CONTACT SENSING AND MONITORING

(75) Inventors: Ronald S. Kolarovic, Cinnaminson, NJ (US); Barry E. Barsky, Huntington Valley, PA (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 10/068,625

(22) Filed: Feb. 6, 2002

(65) Prior Publication Data

US 2002/0173696 A1 Nov. 21, 2002

Related U.S. Application Data

(60) Provisional application No. 60/266,793, filed on Feb. 6, 2001.

(51) Int. Cl.[7] ............................. A61G 11/00; A61B 5/08
(52) U.S. Cl. ..................... 600/22; 600/534; 600/529
(58) Field of Search ........................ 600/22, 300, 301, 600/529, 534, 484, 549, 483, 410, 27, 537, 407, 595, 323; 340/573.1, 575, 457, 667; 5/655; 128/920, 903; 273/3, 14; 454/195; 704/276; 327/309

(56) References Cited

U.S. PATENT DOCUMENTS

| | | | | | |
|---|---|---|---|---|---|
| 4,494,553 | A | * | 1/1985 | Sciarra et al. | 600/534 |
| 4,724,386 | A | * | 2/1988 | Haacke et al. | 324/309 |
| 4,972,842 | A | * | 11/1990 | Korten et al. | 600/529 |
| 5,197,490 | A | * | 3/1993 | Steiner et al. | 600/595 |
| 5,385,529 | A | * | 1/1995 | Koch | 600/22 |
| 5,415,618 | A | * | 5/1995 | Koch | 600/22 |
| 5,505,199 | A | * | 4/1996 | Kim | 600/323 |
| 5,730,355 | A | * | 3/1998 | Lessard et al. | 237/3 |
| 5,871,013 | A | * | 2/1999 | Wainer et al. | 600/407 |
| 6,011,477 | A | * | 1/2000 | Teodorescu et al. | 340/573.1 |
| 6,104,293 | A | * | 8/2000 | Rossi | 340/573.1 |
| 6,171,237 | B1 | * | 1/2001 | Avitall et al. | 600/300 |
| 6,280,392 | B1 | * | 8/2001 | Yoshimi et al. | 600/534 |
| 6,409,654 | B1 | * | 6/2002 | McClain | 600/22 |
| 2001/0044588 | A1 | * | 11/2001 | Mault | 600/549 |

* cited by examiner

Primary Examiner—Eric F. Winakur
Assistant Examiner—Nikita R Veniaminov
(74) Attorney, Agent, or Firm—Barnes & Thornburg

(57) ABSTRACT

An infant care unit of the type comprising means for controlling the environment in which the infant resides includes one or more sensors spaced apart from the infant to sense a physiological parameter and provide a sensor output, the controlling means being responsive to the sensor output to change the environment or provide an alarm or other indication of the parameter. The sensors include one or more of an infrared sensor for sensing the infant's temperature, cameras coupled to video processing software for sensing respiration rate, heart rate or skin perfusion, microphones coupled to audio processing software for sensing respiration rate, breathing difficulty, or infant distress. Speakers are provided for cancelling noise or providing audio signals to the infant. The camera, microphone and speakers are capable of being coupled to a computer network for remote monitoring of the infant.

16 Claims, 3 Drawing Sheets

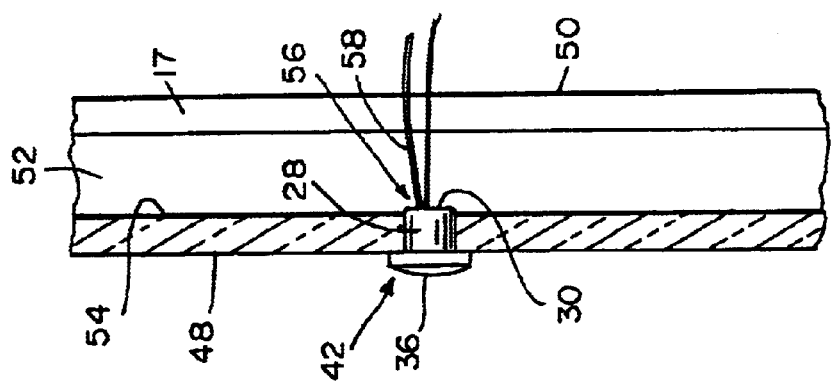
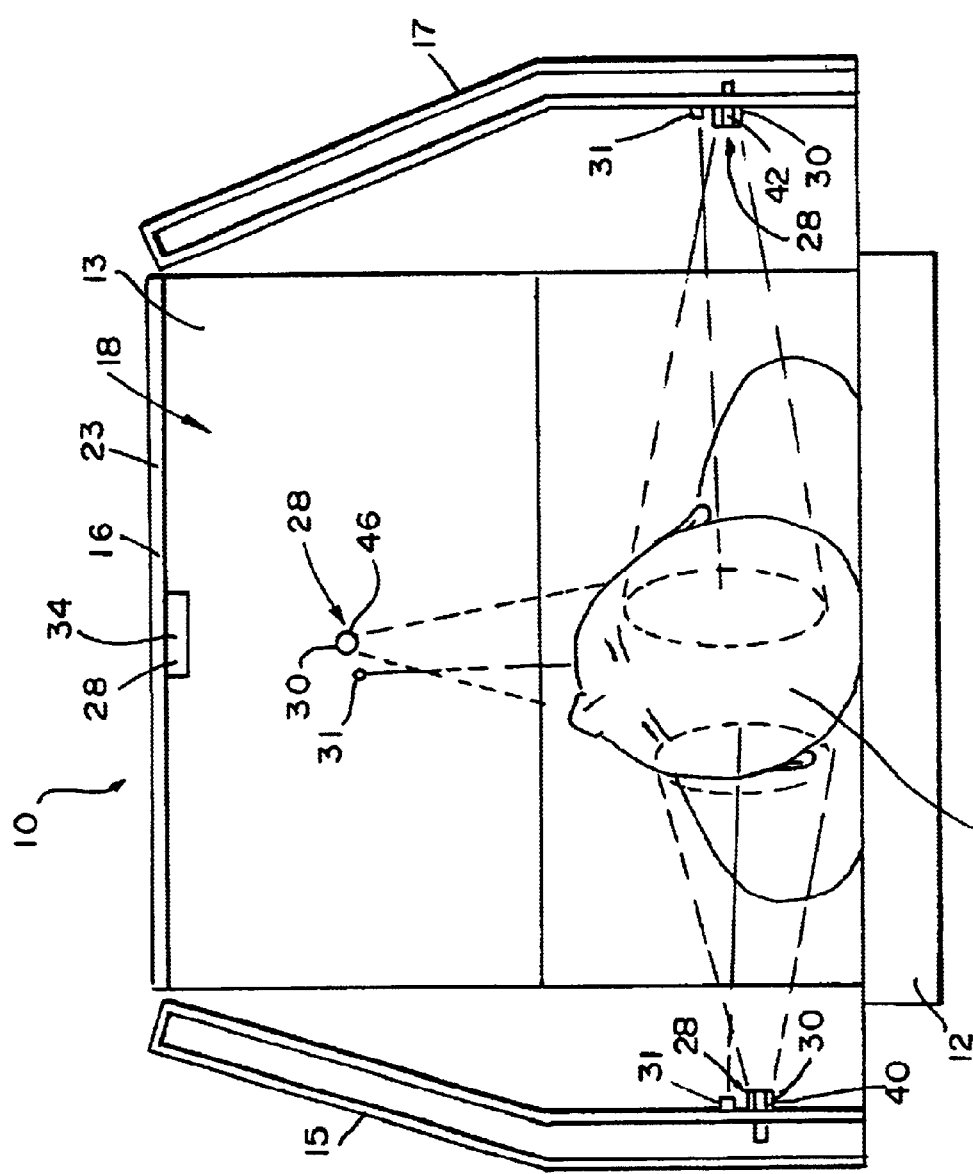

INFANT INCUBATOR WITH NON-CONTACT SENSING AND MONITORING

This Application claims benefit of Provisional No. 60/266,793 filed Feb. 6, 2001.

BACKGROUND AND SUMMARY OF THE INVENTION

The present invention relates generally to incubators and more particularly to incubators having non-contact sensing of physiological parameters and monitoring of an infant contained therein.

It is known to control the temperature of the air adjacent an infant in an incubator. It is also known to circulate the air within an incubator with a blower driven by a motor and to vary the blower speed based on the temperature of the air within the incubator. Thermistors for sensing air temperature and motor controllers are known and have been used to control the temperature of the air adjacent an infant in an incubator and to reduce the blower speed and thereby the associated noise in the enclosure. It is also known to attach transducers to infants in an incubator to directly measure the infants temperature, respiration rate, pulse, and other physiological parameters.

The attachment of transducers to infants creates several problems, including the inadvertent detachment of the transducer by infant movement, and limitation of infant movement.

The infant incubator having means for controlling the environment in which the infant resides disclosed herein includes an infant support surface disposed within an enclosure having a canopy, a sensor spaced apart from the infant to sense a physiological condition and provide a sensor output, and a controlling means responsive to the sensor output to change the environment.

Additional features of the invention will become apparent to those skilled in the art upon consideration of the following detailed description of a preferred embodiment exemplifying the best mode of carrying out the invention as presently perceived.

BRIEF DESCRIPTION OF THE DRAWINGS

In describing the disclosed invention reference will be made to the drawings in which:

FIG. 2 is a partial sectional view taken along line 2—2 of FIG. 1 showing infrared sensors mounted in the side walls and end walls of the canopy of the incubator with their field of sensitivity encompassing the region of the platform on which the infant is held;

FIG. 3 is a sectional view of a wall of the incubator of FIG. 1 showing an infrared sensor with a lens mounted to an internal wall of the canopy.

DETAILED DESCRIPTION OF THE DRAWINGS

Figure 1:
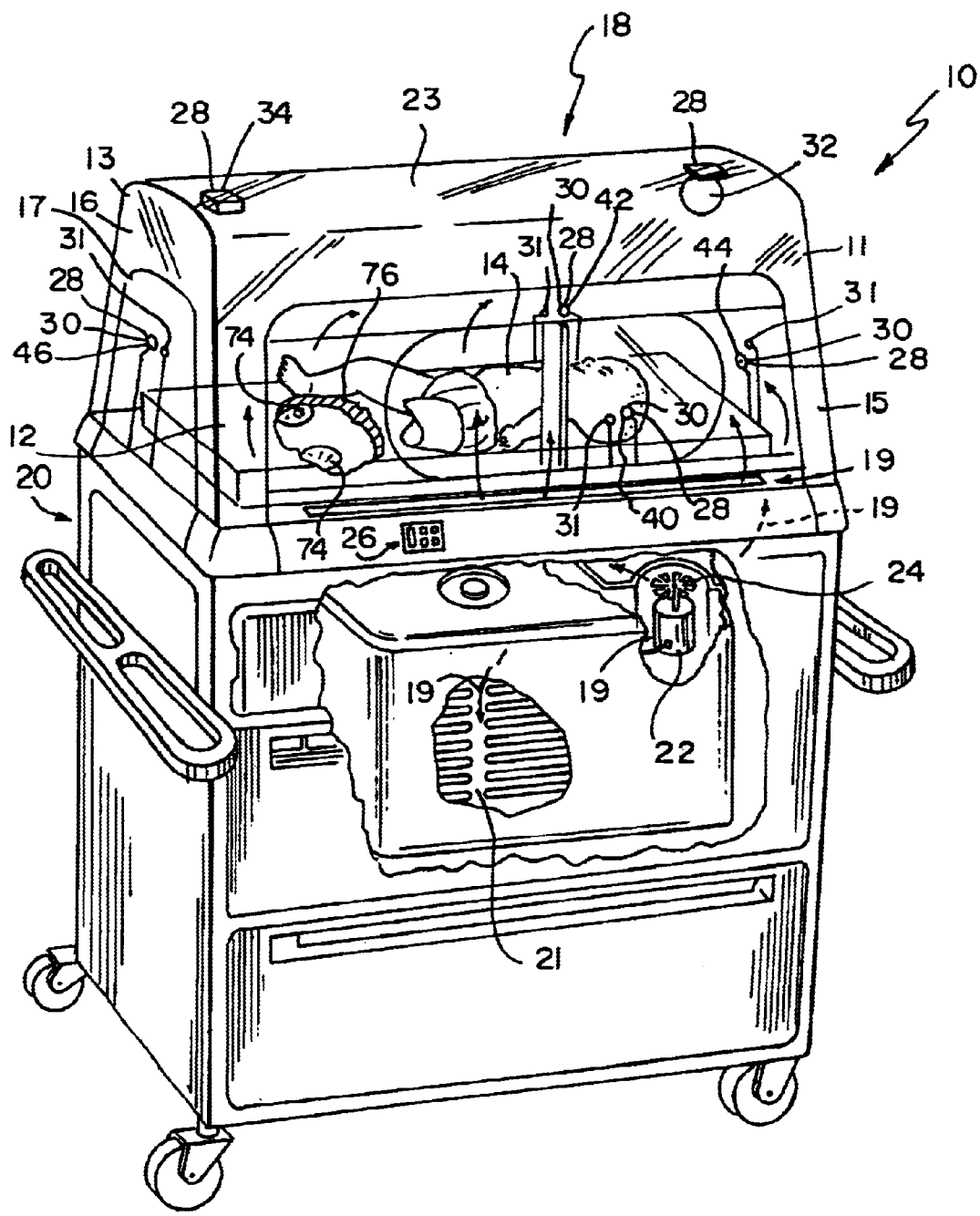
FIG. 1 is a perspective view with parts broken away of an infant incubator having non-contact sensors for monitoring physiological parameters of an infant contained therein showing a video camera mounted to a canopy of the incubator aimed at a platform on which the infant is held, infrared sensors mounted to the canopy arranged so that their field of sensitivity encompasses the region of the platform on which the infant is held, a microphone mounted to the enclosure for audibly sensing the infant, a speaker disposed to provide audio to the interior of the enclosure.
Figure 4:
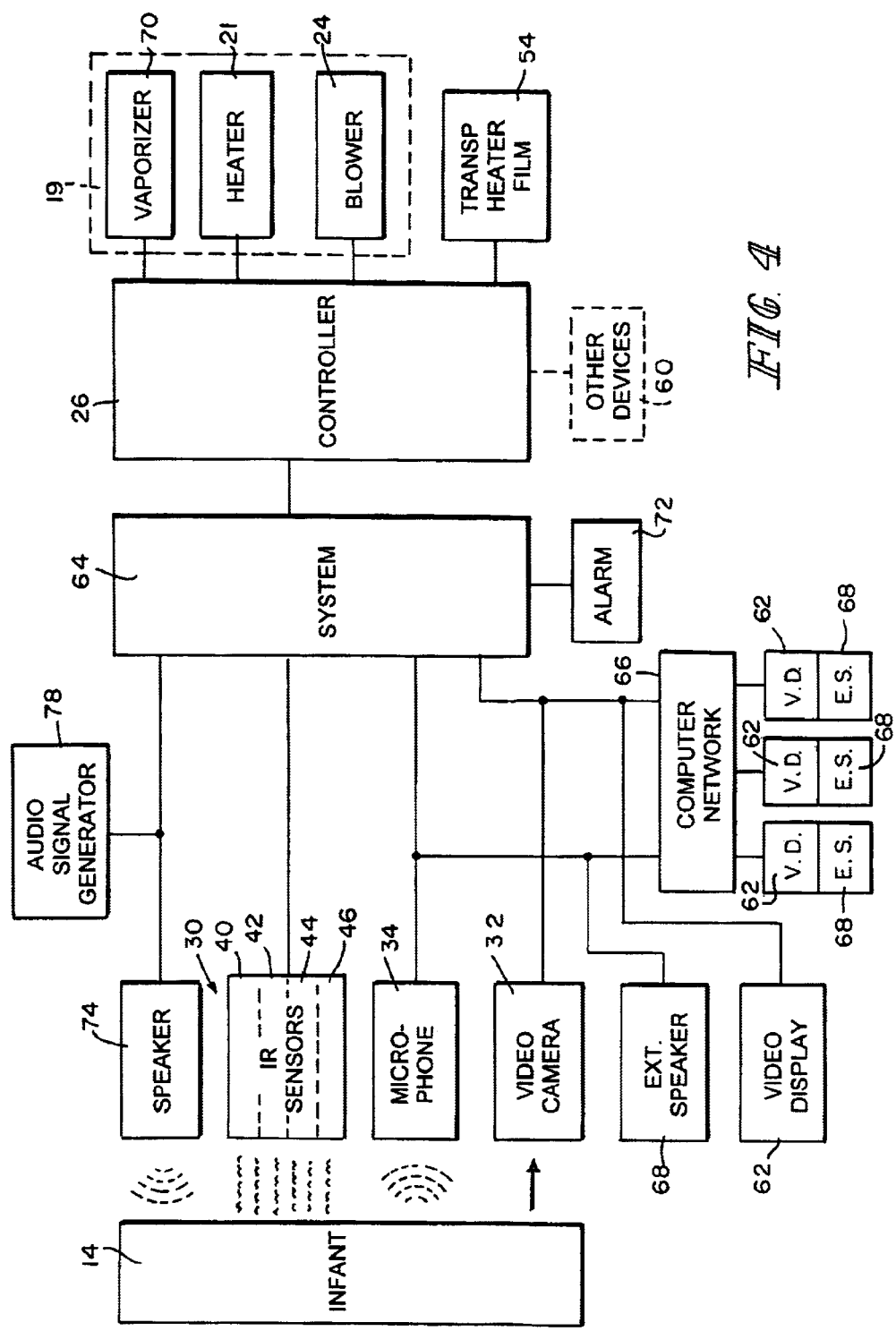
FIG. 4 is a diagrammatic view of the non-contact sensing and monitoring components of the incubator of FIG. 1, showing incubator components controlled in response to signals received from the non-contact sensors and monitors, and a system for correlating the signals from the non-contact sensors to provide appropriate control signals to the controlled incubator components, and remote monitoring stations receiving feeds from the non-contact sensors and monitors.

Incubators and infant warmers are enclosures used to maintain the oxygen content, relative humidity, and air temperature surrounding an infant or baby at appropriate levels. Incubators are well known in the art and are described in Moffett et al., U.S. Pat. No. 5,224,923, McDonough, U.S. Pat. No. 5,242,375, Storti et al. U.S. Pat. No. 5,330,415, Miller et al., U.S. Pat. No. 5,336,156, Lessard et al., U.S. Pat. No. 5,730,355, the disclosures of which are incorporated herein by this reference. Incubators typically include one or more devices for regulating and sensing the temperature, flow, oxygen content, and relative humidity of the air in the incubator and for sensing the temperature, respiration rate, pulse rate and other physiological parameters of an infant in an effort to properly control the environment within the incubator.

The incubator 10 disclosed herein, improves the environment within the enclosure 18 of the incubator 10 by reducing noise in the enclosure 18 and eliminating several sensors and associated lead wires within the enclosure 18 which may be inhibitive to infant 14 movement or may be dislodged by such movement. The disclosed incubator 10 replaces several contact transducers for measuring physiological functions of an infant 14 within the enclosure 18 with non-contact sensors 28 for measuring the same physiological functions of the infant 14. The word "sensor" when used herein in the phrase "non-contact sensor" is intended to have the broadest possible definition. For example, while some of those skilled in the art might not normally associate a video camera as being a sensor, a video camera is within the definition of the term "sensor" as used herein.

The disclosed embodiment of incubator 10 includes a platform 12 for receiving an infant 14, a canopy 16 forming an enclosure or chamber 18 around the platform 12, and a base 20. Canopy 16 includes a head end wall 11, foot end wall 13, side wall 15, side wall 17 and top wall 23. Illustratively walls 11, 13, 15, 17 and 23 are formed from transparent material to facilitate viewing of infant 14. It will be appreciated that incubator 10 may be provided in a variety of styles and designs. See Donnelly et al., U.S. Pat. No. 5,453,077; Goldgerg et al., U.S. Pat. No. 5,759,149; Donnelly et al., U.S. Pat. No. 5,817,002; Moll et al. U.S. Pat. No. 5,817,003; Newkirk et al., U.S. Pat. No. 5,971,913; Donnelly et al., U.S. Pat. No. 5,971,914; Goldgerg et al., U.S. Pat. No. 6,024,694; Goldberg et al., U.S. Pat. No. 6,036,634; Goldgerg et al., U.S. Pat. No. 6,022,310; Speraw et al., U.S. Pat. No. 6,071,228; Prows et al., U.S. Pat. No. 6,049,924; and Copending U.S. application Ser. Nos. 09/571,449 and 09/533,531; the disclosures of which are incorporated herein by this reference.

As shown for example in FIG. 1, infant 14 is held within enclosure 18 resting upon platform 12. Incubator 10 provides a controlled environment for the infant 14 and includes an air circulation system 19 comprising a heater 21 and a blower 24 driven by a blower motor 22. Blower 24 circulates warm air in the enclosure 18 (as shown by unnumbered arrows in FIG. 1) with the air being moved at a flow rate governed by the speed of the blower motor 22. A control system 26 regulates the air circulation system 19.

Sensors 28 are mounted to the canopy so that their field of sensitivity encompasses a portion of platform 12 upon which infant 14 is located. Illustratively, sensors 28 include infra-red sensors 30, video camera 32, and microphone 34. Infrared sensors 30 are capable of remotely sensing the skin temperature of the infant 14. Video camera 32 produces a video feed facilitating remote video monitoring of infant 14. Microphone 34 produces an audio feed facilitating remote audio monitoring of infant 14.

As shown, for example, in FIGS. 1–3, infra-red sensors 30 are illustratively mounted to the walls 11, 13, 15 and 17 of the canopy oriented so that their field of sensitivity includes the area in which an infant 14 is positioned on platform 12 of incubator 10. Illustratively, lenses 36 are positioned adjacent the infrared sensors 30 to concentrate the sensed temperature on the sensor 30. It is within the teaching of the disclosure for sensors without lenses or sensors having lenses and filters incorporated therein to be used in practicing the invention. In the illustrated embodiment, sensors 30 are located at a low level on the side and end walls 11, 13, 15, and 17 of the canopy 16 at a position above the platform on which the infant 14 rests. This positioning of the sensors 30, places the sensors 30 in close proximity to the infant 14. Gluck, U.S. Pat. No. 5,386,831 and Fraden, U.S. Pat. No. 6,129,673 and the prior art cited therein establish the nature of infrared sensors of the type which may be used in incubator 10. The disclosures of these patents and the prior art cited therein are incorporated herein by this reference. Other examples of infrared sensors that may be used within the scope of the invention are Thermalert sensors from Raytek Corporation, ZTP thermopile sensors from Thermometrics Global Business, OS101 Sensors from Omega.com, and miniIRT® from Ircon, Inc.

When a Thermalert sensor is used as infrared sensor 30, such as a TXSLTCF1L2, a laser sight is provided with the unit. The laser sight is used to shine a small beam onto the infant 14 to locate the infant 14 in a position for the IR sensors 30 to monitor temperature. When an IR sensor 30 not incorporating a laser is used, a very low power laser diode 31 adjacent to the IR temperature sensor 30 may be provided within the scope of the disclosure. It is within the teaching of the disclosure for laser 31 to be constantly on or only activated on a temporary basis to properly locate the infant 14. After the infant 14 is located, the imaging system could sound an alarm if the infant 14 moves too far away from the original placement. To reduce infant movement which would trigger the alarm, mattress or infant support pad 76 is formed of a material such as slow recovery foam to conform to the infant. Alternatively, infant placement devices can be used within the teaching of the disclosure.

In the illustrated embodiment, a plurality of infra-red sensors 30 are mounted in the walls 11, 13, 15, and 17 of the canopy 16. Infra-red sensor 40 is mounted on a first side wall 15 of the canopy 16, infra-red sensor 42 is mounted on a second side wall 17 of the canopy 16, infra-red sensor 44 is mounted on head end wall 11 of the canopy and infra-red sensor 46 is mounted on foot end wall 13 of canopy 16. Illustratively, infra-red sensors 40, 42, and 44 are aimed at different locations on the head of the infant, and infra-red sensor 46 is aimed at the torso of the infant 14. Thus, sensors 40, 42, 44 and 46 provide signals indicative of the skin temperature at different locations on the body of the infant 14. It is within the teaching of the disclosure for fewer or more infra-red sensors 30 to be mounted on the canopy 16 of the incubator 10, each aimed at the same or a different location on the infant's body.

As shown, for example, in FIG. 3, second side wall 17 of canopy 16 includes an interior transparent panel 48 and an exterior transparent panel 50. An air space 52 is disposed between interior and exterior transparent panels 48 and 50. Illustratively, a transparent heater film 54 is mounted to the exterior side of interior transparent panel 48 to aid in heating the air in the interior of the enclosure 18. Infra-red sensor 42 is mounted within an aperture 56 formed in interior transparent panel 48. Leads 58 of infra-red sensor 42 extend through exterior transparent panel 50 and are coupled to a controller 26. Lens 36 is mounted to the interior side of interior transparent panel 48 to focus infra-red radiation emanating from the infant 14 onto infra-red sensor 42. It will be understood that infra-red sensors 40, 44, 46 and any additional infra-red sensors 30 may be mounted to the canopy 16 in a similar manner. It will also be understood that infra-red sensor 30 may be mounted to canopy 16 in other known fashions within the teaching of the disclosure.

The temperature signals generated by infra-red sensors 40, 42, 44, 46 are coupled to controller 26 configured to control the temperature of the infant 14 within set parameters. Error signals are operatively connected to the heater 21, blower 24 and heater film 54 facilitating adjustment of the environment in which the infant resides. Controller 26 may also control other devices 60 to facilitate adjustment of the environment in which the infant resides within the teaching of the disclosure. For example, controller 26 may be operatively coupled to resistive heating elements encapsulated in the canopy 16 or platform 12 of the incubator 10, heat lamps, heated fluid circulating systems, or other warmers within the teaching of the disclosure.

Illustratively, video camera 32 is mounted to top wall 23 of canopy 16. Video camera 32 generates a video feed which is coupled to remote video display units 62 and systems. Video camera 32 is coupled to a system 64, such as a computer running video signal processing software capable of monitoring physical parameters of infant 14 in incubator 10. Video signal processing software, capable of analyzing the video feed to determine the respiration rate of infant 14 is incorporated into system 16. Illustratively, this software analyzes the video signal by capturing and comparing frames to determine the number of rises and falls of the infant's chest to determine respiration rate. It is within the teaching of the disclosure for video signal processing software to analyze other aspects of the video feed to determine respiration rate.

It is within the teaching of the disclosure as presently perceived to monitor other physiological parameters using video camera 32. For example, skin color provides an indication of oxygen intake, blood circulation, and temperature of an infant. Software correlating skin color with these physiological parameters may be incorporated into the disclosed device within the teaching of this disclosure. It is also within the teaching of the disclosure to provide an infra-red camera providing an infra-red video feed which may be correlated to determine temperature of infant 14 within incubator 10.

While camera 32 is illustrated as being mounted to the interior of top wall 23 of canopy 16, it is within the teaching of this disclosure to mount camera elsewhere within enclosure 18 or outside of enclosure 18 so long as the field of view of camera 32 includes a portion of platform 12 on which infant 14 rests. Also, other transducers capable of generating a video feed may be substituted for camera 32 within the scope of the disclosure.

The video feed from video camera 32 and audio feed from microphone 34 is coupled through an appropriate interface to a computer network 66. Through the network 66, interested persons, such as health care providers, friends and relatives can monitor the infant at remote locations. It is within the teaching of the disclosure to provide live video and audio feeds of an infant 14 over the internet.

Microphone 34 provides an audio feed from the interior of the enclosure 18. This audio feed is coupled to external speakers 68 for human monitoring of the infant 14. Microphone 34 is also illustratively coupled to system 64 for automated monitoring of physiological parameters of the infant 14. Illustratively, system 64 is a computer running audio signal processing software capable of monitoring physical parameters of infant 14 in incubator 10. Audio signal processing software, capable of analyzing the audio feed to determine the respiration rate of infant 14 is incorporated into system. Illustratively, this software analyzes the audio feed to determine the number of times infant 14 inhales and exhales to determine respiration rate. It is within the teaching of the disclosure for audio signal processing software to analyze other aspects of the audio feed to determine respiration rate.

It is within the teaching of the disclosure as presently perceived to monitor other physiological parameters using microphone 34. For example, the audio feed produced by an infant, who is wheezing is distinguishable from the audio feed produced by a normally breathing infant. When an infant has been diagnosed as having a respiratory disorder capable of medication by vaporizing medicine, the system may be coupled through controller 26 to a vaporizer 70 for releasing vaporized medicine into the circulated air upon detection of wheezing by the audio signal processing software. If an infant has not been previously diagnosed with a respiratory disorder, detection of wheezing by the audio signal processing software triggers an alarm. Other conditions detected by audio signal processing software, eg. crying, cessation of respiration, coughing, choking, can also trigger an alarm 72 or a controlled response of incubator 10 within the teaching of the disclosure. Such alarm 72 may include an audible alarm, such as activation of a buzzer or siren, visual alarm, such illumination of an indicator light, or other signal of a condition needing attention within the scope of the disclosure.

A speaker 74 is provided within enclosure 18 to facilitate providing audio to the interior of enclosure 18. Speaker 74 may be mounted anywhere within enclosure 18 within the teaching of the present invention although speaker 74 is illustrated as being encompassed in an infant support pad 76 forming a portion of platform 12. An infant support pad incorporating speakers is disclosed in Shuto et al. U.S. Pat. No. 5,865,771, the disclosure of which is incorporated herein by this reference.

Illustratively, speaker 74 is coupled to an audio signal generator 78. It is within the teaching of the present disclosure for audio signal generator 78 to include an external microphone, a playback device for stored audio signals, an audio feedback device and other devices capable of generating an audio signal. Speaker 74 facilitates the production of soothing or calming noises within the interior of the incubator. Speaker 74 also facilitates providing audio feedback acting as destructive interference to cancel undesirable noises within the interior of the enclosure. For instance, it is known that blower noise may disturb an infant within an incubator, therefore it is within the teaching of this disclosure for speaker 74 to provide a feedback signal of the blower noise in order to cancel blower noise within the interior of the incubator 10.

Illustratively, the audio feed coupled to the speaker 74 is also coupled to the system 64 running the audio signal processing software. This facilitates cancellation of externally provided audio signals so that the audio signal processing software can filter out extrinsic noises and focus on noises generated by infant 14 within the enclosure 18.

It is also within the teaching of the invention to use other non-contact sensors 28 to measure physiological parameters of infant 14 within incubator 10. For example, while not illustrated, an ultrasonic ranging system can be mounted to the enclosure aimed at infant 14. By measuring the time delay for return of signals, the distance to the infant's chest could be determined. As the change in the distance measured from the previous measurement decreases, it can be assumed that the infant is inhaling, as the change in the distance measured from the previous measurement increases, it can be assumed that the infant is exhaling. Appropriate software can correlate these measurements to determine the respiration rate of the infant. Alternatively, the frequency of the returning ultra-sonic wave could be measured, and using the Doppler effect, the respiration rate of the infant could be correlated. It is within the teaching of the invention to use other wave generating and detecting apparatus in a similar manner as that disclosed for the ultrasonic ranging system to measure physiological parameters of an infant using non-contact sensors 28.

Although the invention has been described in detail with reference to a certain illustrated embodiment, variations and modifications exist within the scope and spirit of the invention as described and defined in the following claims.

What is claimed is:

1. An infant care unit comprising:
   means for controlling the environment in which an infant may reside,
   one or more sensors spaced apart from the infant to sense a physiological parameter of the infant and provide a sensor output, the controlling means being responsive to the sensor output to change the environment or provide an alarm or other indication of the parameter; and
   a respiration sensor adapted to be out of physical contact with the infant for determining the respiration rate of the infant, the respiration sensor being a device having a field of vision including a portion of the infant and generating a video feed.

2. The infant care unit of claim 1 comprising a temperature sensor adapted to be spaced out of physical contact with the infant to determine the temperature of the infant.

3. The infant care unit of claim 2 which the temperature sensor is an IR sensor.

4. The infant care unit of claim 2 comprising a system for heating the environment in which an infant may reside and a control system for the heating system, the control system being operatively connected to the temperature sensor.

5. The infant care unit of claim 1 comprising a plurality of temperature sensors adapted to be spaced about and out of physical contact with the infant to determine the temperature of the infant.

6. The infant care unit of claim 5 in which each temperature sensor is an IR sensor.

7. The infant care unit of claim 6 comprising side and end walls adapted to be spaced about the infant and providing an enclosure, the IR temperature sensors being positioned on the side and end walls.

8. An infant care unit comprising:
   an enclosure in which an infant may reside,
   means for controlling the environment in the enclosure,
   one or more sensors spaced apart from the infant to sense a physiological parameter of the infant and provide a sensor output, the controlling means being responsive to the sensor output to change the environment or provide an alarm or other indication of the parameter, and a respiration sensor adapted to be out of physical contact with the infant for determining the respiration rate of the infant, the respiration sensor being a device generating an audio feed of sounds within the enclosure.

9. The infant care unit of claim 8 comprising a temperature sensor adapted to be spaced out of physical contact with the infant to determine the temperature of the infant.

10. The infant care unit of claim 9 in which the temperature sensor is an IR sensor.

11. The infant care unit of claim 9 comprising a system for heating the environment in the enclosure and a control system for the heating system, the control system being operatively connected to the temperature sensor.

12. The infant care unit of claim 8 comprising a plurality of temperature sensors adapted to be spaced about and out of physical contact with the infant to determine the temperature of the infant.

13. The infant care unit of claim 12 in which each temperature sensor is an IR sensor.

14. The infant care unit of claim 13 comprising side and end walls adapted to be spaced about the infant and providing an enclosure, the IR temperature sensors being positioned on the side and end walls.

15. The infant care unit of claim 8 and further comprising a speaker located within the enclosure and coupled to a sound generating device for generating sounds within the enclosure.

16. The infant care unit of claim 15 wherein the sound generating device includes a feedback device for feeding the audio feed to the speaker to cancel noise within the enclosure.

* * * * *